US009681950B2

(12) United States Patent
Richter et al.

(10) Patent No.: US 9,681,950 B2
(45) Date of Patent: Jun. 20, 2017

(54) SYSTEM AND METHOD FOR PLACING A PERCUTANEOUS VALVE DEVICE

(75) Inventors: Yoram Richter, Ramat Hasharon (IL); Jacob Richter, Arsuf (IL)

(73) Assignee: Valve Medical Ltd., Tel Aviv (IL)

( * ) Notice: Subject to any disclaimer, the term of this patent is extended or adjusted under 35 U.S.C. 154(b) by 1216 days.

(21) Appl. No.: 12/686,337

(22) Filed: Jan. 12, 2010

(65) Prior Publication Data

US 2010/0179648 A1    Jul. 15, 2010

Related U.S. Application Data

(60) Provisional application No. 61/144,007, filed on Jan. 12, 2009.

(51) Int. Cl.
*A61F 2/24*        (2006.01)
(52) U.S. Cl.
CPC .......... *A61F 2/2412* (2013.01); *A61F 2/2439* (2013.01); *A61F 2250/006* (2013.01)
(58) Field of Classification Search
CPC .... A61F 2/2427; A61F 2/2436; A61F 2/2439; A61F 2250/006; A61F 2/2412; A61F 2/24; A61F 2/243; A61F 2/2466
USPC ............................... 623/2.11, 2.17–2.19, 2.38
See application file for complete search history.

(56) References Cited

U.S. PATENT DOCUMENTS

| 5,411,552 | A | | 5/1995 | Andersen et al. |
| 5,584,803 | A | * | 12/1996 | Stevens ............... A61B 17/29 604/101.01 |
| 5,800,531 | A | * | 9/1998 | Cosgrove et al. .......... 623/2.11 |
| 5,840,081 | A | | 11/1998 | Andersen et al. |
| 5,868,762 | A | | 2/1999 | Cragg et al. |
| 5,891,160 | A | * | 4/1999 | Williamson et al. ......... 606/144 |
| 5,928,250 | A | | 7/1999 | Koike et al. |
| 6,042,601 | A | | 3/2000 | Smith et al. |

(Continued)

FOREIGN PATENT DOCUMENTS

| RU | 2200507 C2 | 3/2003 |
| WO | WO 2007/009117 A1 | 1/2007 |
| WO | WO 2007/097983 A2 | 8/2007 |

OTHER PUBLICATIONS

International Search Report from corresponding PCT Application No. PCT/IB2010/000048, 15 pages.

(Continued)

*Primary Examiner* — Alexander Orkin
(74) *Attorney, Agent, or Firm* — Cadwalader Wickersham & Taft LLP

(57) ABSTRACT

A system and process for placing a percutaneous valve device in a body lumen at the location of implantation is provided, which enhances the accuracy of the placement. Anchors and placement wires are used to fix the implantation target and guide the device to the implantation site. The system and method are applicable to preassembled percutaneous valve devices as well as a modular prosthetic valve device. The modular valve device comprises two or more device modules and is designed to be delivered unassembled and then assembled in the body lumen at or near the site where implantation occurs. The device modules may be assembled before or after the implantation target is fixed with the anchor, and then placed using the placement system in a manner similar to how a preassembled percutaneous valve device may be placed in accordance with the invention.

22 Claims, 2 Drawing Sheets

(56) References Cited

U.S. PATENT DOCUMENTS

| | | | |
|---|---|---|---|
| 6,056,760 A | 5/2000 | Koike et al. | |
| 6,168,614 B1 | 1/2001 | Andersen et al. | |
| 6,312,464 B1* | 11/2001 | Navia | A61F 2/2427 128/898 |
| 6,893,460 B2 | 5/2005 | Spenser et al. | |
| 7,597,711 B2* | 10/2009 | Drews et al. | 623/2.11 |
| 7,618,449 B2* | 11/2009 | Tremulis et al. | 623/2.11 |
| 8,083,793 B2* | 12/2011 | Lane et al. | 623/2.38 |
| 2002/0013621 A1* | 1/2002 | Stobie et al. | 623/2.11 |
| 2004/0138741 A1 | 7/2004 | Stobie et al. | |
| 2005/0075584 A1* | 4/2005 | Cali | 600/587 |
| 2005/0283231 A1 | 12/2005 | Haug et al. | |
| 2006/0135967 A1* | 6/2006 | Realyvasquez | A61B 17/072 606/142 |
| 2006/0195184 A1 | 8/2006 | Lane et al. | |
| 2006/0195185 A1 | 8/2006 | Lane et al. | |
| 2006/0287717 A1 | 12/2006 | Rowe et al. | |
| 2007/0016288 A1 | 1/2007 | Gurskis et al. | |
| 2007/0255398 A1 | 11/2007 | Yang et al. | |
| 2007/0260305 A1 | 11/2007 | Drews et al. | |
| 2007/0293942 A1 | 12/2007 | Mirzaee | |
| 2010/0161047 A1* | 6/2010 | Cabiri | 623/2.37 |

OTHER PUBLICATIONS

Webb et al., "Percutaneous Aortic Valve Implantation Retrograde from the Femoral Artery," Circulation 113:842-850 (2006).

Piazza et al., "Early and Persistent Intraventricular Conduction Abnormalities and Requirements for Pacemaking After Percutaneous Replacement of the Aoritc Valve," JACC Cardiovascular Interventions 1(3): 310-315 (2008).

Piazza et al., "Anatomy of the Aortic Valvar Complex and its Implications for Transcatheter Implantation of the Aortic Valve," Circ. Cardiovasc. Interventions 1: 74-81 (2008).

Webb et al., "Percutaneous Suture Edge-to-Edge Repair of the Mitral Valve," EuroIntervention 5: 86-89 (2009).

Eurasian Patent Office Search Report from corresponding Eurasian Application No. 201190038 dated Sep. 6, 2012, 2 pages.

\* cited by examiner

SYSTEM AND METHOD FOR PLACING A PERCUTANEOUS VALVE DEVICE

This application claims benefit of priority of U.S. Provisional Application Ser. No. 61/144,007, filed Jan. 12, 2009.

FIELD OF INVENTION

The present invention relates to prosthetic valve devices for implantation in the body and methods of placement thereof. In particular, the invention relates to a method of placing a valve device in a target location of a body lumen with enhanced accuracy. The invention further relates to placing a multi-component, or modular, prosthetic valve device with enhanced accuracy. The modular prosthetic valve device is a prosthetic valve capable of being delivered in parts and assembled in the body.

BACKGROUND OF THE INVENTION

The human body contains a wide variety of natural valves, such as, for example, heart valves, esophageal and stomach valves, intestinal valves, and valves within the lymphatic system. Natural valves can degenerate for a variety of reasons, such as disease, age, and the like. A malfunctioning valve fails to maintain the bodily fluid flow in a single direction with minimal pressure loss. An example of a malfunctioning valve is a heart valve that may be either stenotic, i.e., the leaflets of the valve are do not open fully, or regurgitant, i.e., the leaflets of the valve do not close properly. It is desirable to restore valve function to regain the proper functioning of the organ with which the valve is associated. For example, proper valve function in the heart ensures that blood flow is maintained in a single direction through a valve with minimal pressure loss, so that blood circulation and pressure can be maintained. Similarly, proper esophageal valve function ensures that acidic gastric secretions do not irritate or permanently damage the esophageal lining.

Several percutaneous prosthetic valve systems have been described. One example described in Andersen, et. al. (U.S. Pat. No. 5,411,552) comprises an expandable stent and a collapsible valve which is mounted onto the stent prior to deployment. The collapsible valve may be a biological valve or it may be made of synthetic material. The Anderson prosthetic valve is delivered and deployed using a balloon catheter which balloon is used to expand the valve-stent prosthesis to its final size. See also, U.S. Pat. No. 6,168,614 (Andersen, et al.) entitled "Valve Prosthesis for Implantation in the Body" and U.S. Pat. No. 5,840,081 (Andersen, et al.) entitled "System and Method for Implanting Cardiac Valves."

Spenser, et. al. (U.S. Pat. No. 6,893,460) describe another prosthetic valve device comprising a valve structure made of biological or synthetic material and a supporting structure, such as a stent. The Spenser prosthetic valve is a crimpable leafed-valve assembly consisting of a conduit having an inlet and an outlet, made of pliant material arranged to present collapsible walls at the outlet. The valve assembly is affixed to the support stent prior to deployment. The complete valve device is deployed at a target location within the body duct using a deploying means, such as a balloon catheter or a similar device.

Accurate placement of current percutaneous valve devices relative to the existing native anatomy is often problematic, particularly in the case of aortic valve replacements. A prosthetic aortic valve that is placed too distally (relative to the heart, i.e., toward the aorta) can occlude or impede flow into the orifices of the coronary arteries. For example, depending on the position of the coronary ostia, either the skirt of the prosthetic valve or large native valve leaflets, when pressed down against the aorta wall, may physically or functionally obstruct the orifices and impede coronary arterial flow. See, e.g., Piazza, N., et al., "Anatomy of the Aortic Valvar Complex and Its Implications for Transcatheter Implantation of the Aortic Valve," CIRCULATION CARDIOVASCULAR INTERVENTIONS, 1:74-81 (2008); Webb, J G, et al., "Percutaneous aortic valve implantation retrograde from the femoral artery," CIRCULATION, 113:842-850 (2006). This obstruction may be either physical or it may be functional, i.e., the orifices of the coronary arteries are physically patent, but due to alterations in flow patterns produced by the prosthetic valve, flow into the coronary arteries is partially impeded. A prosthetic valve that is placed too proximally (i.e., toward the ventricular outflow tracts of the left ventricle) can interfere with the anterior leaflet of the Mitral valve, the atrioventricular node, or the bundle of His (conduction tissues). Approximately thirty percent of patients receiving prosthetic valves percutaneously require pacemakers, because the valve is placed with the ventricular end too close to or on top of the left bundle branch, putting pressure on the electrical conduction apparatus. See, e.g., Piazza, N., et al., "Early and persistent intraventricular conduction abnormalities and requirements for pacemaking following percutaneous replacement of the aortic valve," JACC CARDIOVASCULAR INTERVENTIONS, 1:310-316 (2008); Piazza, N., et al., "Anatomy of the Aortic Valvar Complex and Its Implications for Transcatheter Implantation of the Aortic Valve," CIRCULATION CARDIOVASCULAR INTERVENTIONS, 1:74-81 (2008).

Therefore, a need exists for improved placement and more simplified delivery of artificial valves and to increase the safety and accuracy of the percutaneous valve replacement procedure.

It is an object of the invention to provide a system and method of accurately placing a prosthetic valve device percutaneously in a lumen. Another object of the invention is to provide accurate placement of a prosthetic valve device that is minimally invasive.

SUMMARY OF THE INVENTION

The present invention relates to a system and method for positioning and placing an endovascular prosthetic valve device at a desired location of implantation, with improved accuracy. The method involves fixing one or more small anchors such as leading sutures or locating devices to the native anatomy of the lumen where the valve device is to be implanted, and using them to guide the placement of a prosthetic valve devices to the desired location. Depending on the type of anchor, the anchor may directly engage a portion of the valve device, or the anchor may be threaded through a portion of the valve device to guide the threaded portion to the site of implantation, or the anchor may be attached to a placement wire, which placement wire may be threaded through a portion of the valve device to guide the threaded portion along the placement wire toward the anchor, i.e., to the site of implantation. The anchors may also be used to fix the valve device in place.

The system and method of the invention are applicable not only to single unit percutaneous valve devices and those percutaneous valve devices assembled before delivery—as described in, for example, U.S. Pat. Nos. 5,411,552 and 6,893,460 (representative of types of valve devices referred to herein as "pre-assembled" valve devices), but also to the lower profile, modular (multi-component) valve device, or valve assembly, described herein.

For delivery of either the modular valve device or pre-assembled valve device, the anchor is preferably operably connected to a portion of the valve device that is to be guided to the implantation site to seat the device, such as the frame of the valve device.

The system and method of placing a prosthetic valve device percutaneously in a lumen confers improved accuracy of placement, simplified procedure, and increased efficacy. This permits such procedures to be performed in smaller and less sophisticated medical facilities with increased safety and superior results, thereby expanding the number of medical facilities equipped to perform percutaneous valve replacement procedures.

BRIEF DESCRIPTION OF THE DRAWINGS

FIG. 1A depicts the anchors fixed to the aorta wall. FIG. 1B depicts the anchors fixed to the aortic surface of the native valve leaflets. FIG. 1C depicts the anchors fixed to the ventricular surface of the native valve leaflets.

DETAILED DESCRIPTION OF THE INVENTION

Figure 1:
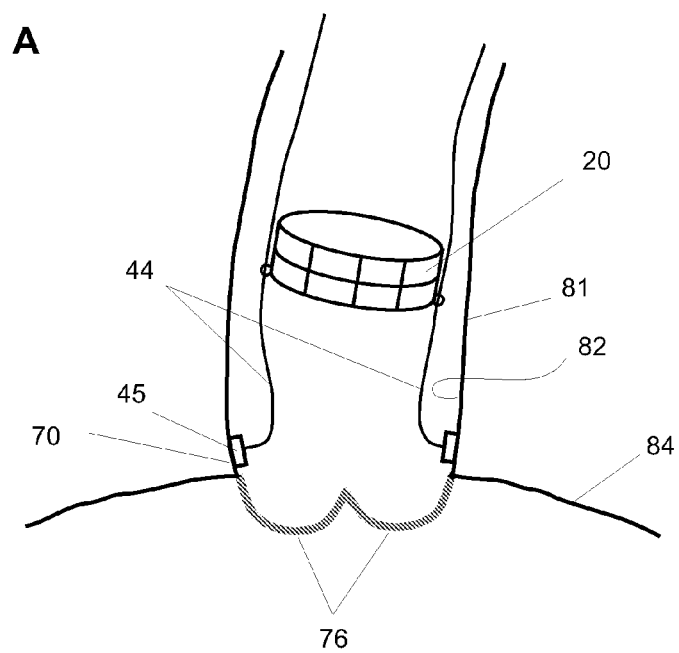
FIGS. 1A-1C illustrate three aspects of a system and method of placing a valve device at a desired location in a lumen using anchors and, in this embodiment, placement wires. In particular, different positions on the native anatomy where the anchors may be affixed to improve valve placement accuracy are illustrated.
Figure 1:
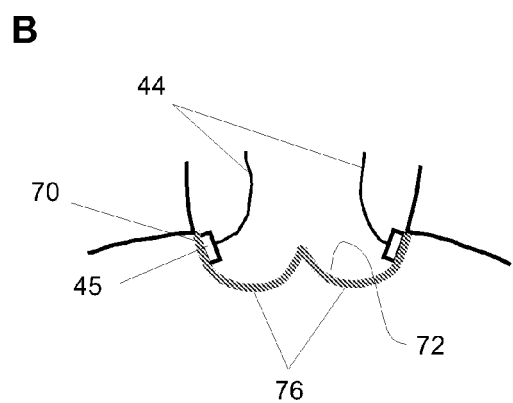
Figure 1:
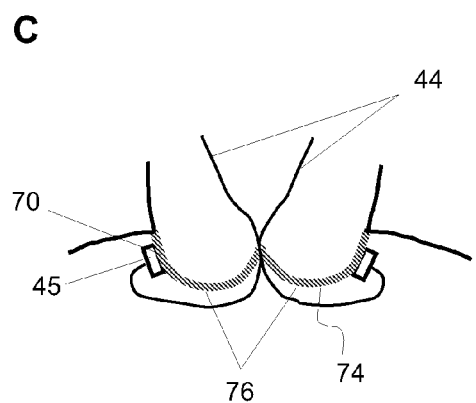

The present invention provides a system for improved positioning of a valve device in a body lumen and a method for facilitating accurate positioning of a percutaneous valve device in a body lumen. Use of the system and methods of the invention is expected to improve outcomes and minimize complications and shorten hospital stays. Further, the method is expected to reduce patient trauma, simplify the procedure, and make the procedure available to more patients and more hospitals.

The invention provides a system and method for accurate placement of implantable percutaneous prosthetic valve devices, systems and methods for percutaneously delivering and deploying implantable prosthetic heart valve devices and other implantable percutaneous prosthetic valve devices in body lumens. The placement system comprises the prosthetic valve device, an anchor, and a delivery device. The anchor is used to place the valve device at the desired location of valve implantation. Therefore, the anchor may first be placed at the desired site of valve implantation and then the valve device may be guided to that site. In this manner, the precise location of implantation may be chosen carefully and the anchor affixed or the location of the anchor adjusted. Then once the anchor is affixed, the prosthetic valve may be more efficiently placed and implanted, improving accuracy.

In some embodiments, where the anchor is, for example, a hook or rivet, the system may further include a placement wire which is attached to the anchor. The placement wire may have free ends for threading through a portion of valve device. In embodiments where the anchor is a leading suture, the leading suture may be threaded through a portion of the valve device. In further embodiments, the placement wire or leading suture may be threaded through part of the delivery system, such as the expansion balloon or system used for self-expanding support structures. The placement wire and leading suture are used to guide the prosthetic valve wire to the site of implantation. In each of these embodiments, the threaded portion of the valve device may include loops or specific holes through which the placement wire or leading suture may be threaded, and may be the proximal edge (ventricle side) of the valve material. Alternatively, the threaded portion may inherently have open spaces for threading the placement wire or leading suture—for example, as on a support structure such as a stent. In still another embodiment, the anchor may be a docking apparatus and the portion of the valve device may have an anchor interface unit. In this embodiment, the anchor may directly engage a portion of the valve device.

The valve device used with the placement system may be a preassembled percutaneous valve device, such as those described or known in the art. Alternatively, it may be modular percutaneous valve device, comprising a plurality of modules, as described in ¶¶29-30, 32-34, 39-49 and FIGS. 1a-4c of priority U.S. provisional patent application No. 61/144,007, in ¶¶37-47, 60-62, 65-82 and FIGS. 1-6c of co-pending U.S. application Ser. No. 12/686,335 (modular), entitled "Modular Percutaneous Valve Structure and Delivery Method," filed on date even herewith, and in ¶¶27-31, 35-40, 42-46, 48-70 and FIGS. 1-10 (including description of self-assembly members) of co-pending U.S. application Ser. No. 12/686,338 (self-assembly), entitled "Self-Assembling Modular Percutaneous Valve and Methods of Folding, Assembly and Delivery," filed on date even herewith, which applications are incorporated herein by reference.

The system and method of the invention are particularly adapted for use in percutaneous aortic valve replacement, but may also find use as replacements for other cardiac valves, such as, e.g., pulmonic, mitral and tricuspid valves, as well as valves in the peripheral vasculature or in other bodily lumens, such as the alimentary canal, lymph ducts, the biliary duct, and any other lumens having valves requiring replacement or needing valve implantation. Although particularly adapted for use in lumens of the human body, the devices, systems and methods may also find application in animals.

The placement system and method of the invention may be used with pre-assembled, percutaneous prosthetic valves, some of which are commercially available. Examples of such preassembled, percutaneous prosthetic valves are described, for example, in U.S. Pat. Nos. 5,411,552 and 6,893,460, and include, for example, the CoreValve Revalving™ System from Medtronic/CoreValve Inc. (Irvine, Calif., USA), Edwards-Sapien or Cribier-Edwards valves from Edwards Lifesciences (Irvine, Calif., USA), and devices in development by AortTx (Palo Alto, Calif., USA), Sadra Medical, Inc. (Campbell, Calif., USA), Direct Flow Medical (Santa Rosa, Calif., USA), HLT, Inc. (Maple Grove, Minn., USA), ATS Medical, Inc. (Minneapolis, Minn., USA), Advanced BioProsthetic Surfaces (San Antonio, Tex., USA), JenaValve Technology GmbH (Munich, Germany), Ventor Technologies (Netanya, Israel), and Sorin Group (Saluggia, Italy) and any other variations of prosthetic valves mounted on balloon-expandable or self-expanding stents for delivery.

The system and method of the invention are also applicable to a modular prosthetic valve device and system that allows a prosthetic valve device to be delivered safely into a lumen in a reduced diameter delivery device. One embodiment of the modular prosthetic valve device comprises two main device modules: a valve module and a support structure, which are designed to be assembled in the body, for example in the aorta or at the site of implantation. The support structure provides the framework, or backbone, of the device, housing the valve module and holding the valve module in place within the body. The valve module is the device module having the leaflets of the valve device and it provides a conduit having a inlet end and an outlet end.

In one embodiment, the valve module is a valve assembly that further comprises a plurality of valve sections, which may be assembled into the valve assembly in the body. The valve assembly may then be combined with the support structure into the assembled valve device. In another embodiment, the valve module is a one-piece module that is delivered apart from the support structure and is combined with the support structure in the body. The one-piece valve module may be delivered as an unassembled, folded leaflets substructure or unassembled, folded leaflets-ring, and assembled so that it forms a conduit with leaflets prior to combining with the support structure. In an alternative embodiment, the modular valve device may be a valve assembly comprising a plurality of valve sections that may be deployed and assembled into a complete valve device without a support structure. The valve module and support structure are delivered to a desired location in the lumen within an appropriate delivery device such as a catheter, for example an endovascular catheter. Once the device modules are deployed from the delivery device into the lumen, they may be combined to form a fully assembled valve device.

Figure 2:
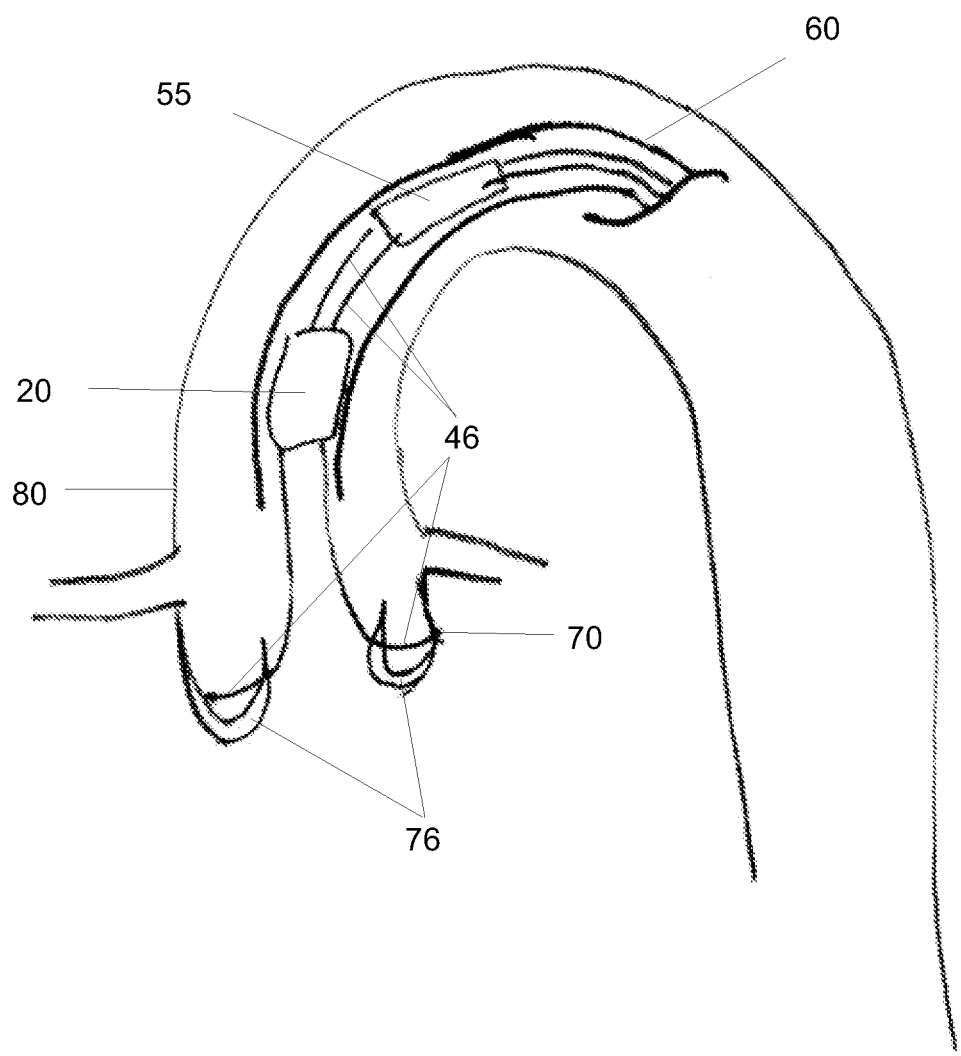
FIG. 2 illustrates a system and method of placing the valve device at a desired location in a lumen, wherein the anchors are leading sutures, positioned at the target site and used to guide the valve device to that position so as to position it with improved accuracy.

The aforementioned embodiments of the placement system and method, as well as other embodiments, delivery and assembly methods, different designs and different types of devices are discussed and explained below with reference to the accompanying drawings. The use and operation of the valve placement embodiments of the invention are illustrated in FIGS. 1A-2. Note that the drawings are provided as an exemplary understanding of the present invention and to schematically illustrate particular embodiments of the present invention. The skilled artisan will readily recognize other similar examples equally within the scope of the invention. The drawings are not intended to limit the scope of the present invention as defined in the appended claims.

It is crucial that a prosthetic valve device is placed in a vessel (or lumen) with precision to ensure proper valve function and safety to the patient. Anchors 45 may be used to guide the delivery of the valve device, or a device module such as a support structure 20 of a modular valve device (as illustrated in FIGS. 1A-1C) to the target site. Accordingly, in one embodiment a placement system according to the invention comprises a prosthetic valve device and one or more anchors 45 and one or more placement wires 44. The placement wires 44 are connected to the anchors 45, as illustrated in FIGS. 1A-1C. In one embodiment, the placement wires 44 may be threaded through and packaged with a device module, such as a support structure 20, of a modular valve device. Alternatively, anchors 45 may be used to guide any portion of the valve device to the target site, in particular with respect to pre-assembled percutaneous valve devices. Thus, for example placement wires 44 may be threaded through the valve portion of the device. With respect to modular valve device, in such an alternative embodiment (not shown), the placement wires 44 may be threaded through the valve module or one or more valve sections, and the valve module may be combined with the support structure 20 prior to guiding the assembled valve device to the location of implantation 70. In another such alternative embodiment (not shown), the placement wires 44 may be threaded through both the support structure 20 and valve module. In yet another embodiment applicable to either pre-assembled or modular valve devices, the placement wires may be threaded through the delivery system.

The anchors 45 are designed to be attached to native tissue in the lumen, specifically at the location of implantation 70. The placement wires 44 and anchors 45 may be used to guide the device module through which it is threaded, such as the support structure 20, and thus modular prosthetic valve device, to the desired location of implantation 70 within a body lumen, for example an aorta 81, with improved accuracy. In another embodiment, where the valve device is pre-assembled, such as a percutaneous valve device in the art, the placement wires may be threaded through a suitable part of the valve device, and used to guide the valve device to the desired location of implantation, similar to FIGS. 1A-1C. The proximal portion of the "free ends" of the placement wires may exit the body at the proximal end of the delivery system, or may be attached to a portion of the delivery system.

Once the anchors 45 are in place, the prosthetic valve device may be guided into place along the placement wires 44 originating from the anchors 45. As shown in FIG. 1A, the support structure 20 may be guided into place along the placement wires 44. In an alternative embodiment, instead of being connected to placement wires, the anchors 45 may include a docking apparatus that may be connected directly to an anchor interface unit attached to the pre-assembled valve device, or support structure 20 of a modular valve device, that allows orientation of the valve device relative to the anchors 45. Anchor docking apparatus and anchor interface unit may be complementary so as to may lock together to secure the valve device at the target site. In accordance with the invention, the support structure may be guided to the site of implantation prior to combining with the valve module, or the modular valve device may be assembled and then guided along the placement wires to be placed at the implantation site. Because it occurs after the delivery and assembly of the modular valve device, this latter embodiment of placing an assembled modular valve device is similar to placing a pre-assembled valve device, such as a percutaneous valve device in the art, in accordance with the invention. Assembly of the modular valve device proceeds as described above, either using a pull wire or a self-assembly member.

In addition to aiding in affixing the valve device to the target site, for example, by effecting "docking" of the device, the anchors 45 also may be used to facilitate attaching the device modules together thus aiding in assembly and triggering the locking mechanisms.

Anchors 45 may include a button or rivet-type device, a hook, a percutaneously-inserted suture, interconnecting geometries, or any other type of docking apparatus device (not shown). Where the anchor includes an anchor docking apparatus, a portion of the valve device comprises an anchor interface unit to engage the anchor docking apparatus. In this embodiment, the anchor directly engages the valve device via the connection between the anchor docking apparatus and the anchor interface unit. The anchor docking apparatus and anchor interface unit combination may be any of male-female coupling type components, slotted hook mechanisms, hook and eye components, hook and groove components, interconnecting geometries (e.g., dovetail), press-fix connectors or similar components within the skill in the art.

In one embodiment, in which the anchors are of the button type, the anchors may be affixed to the native anatomy by puncturing the vessel wall and affixing two parts of the anchor to either side of the vessel. A catheter is used to direct a puncturing tool to the site of the vessel where the anchor is to be placed and the tool is used to create a hole in the vessel wall through which anchors may be affixed. The puncturing tool is removed from the catheter and the catheter is advanced through the newly formed opening in the vessel wall. The anchor is then deployed from the catheter on the outer side of the vessel wall. The catheter is then retracted through the hole and the remainder of the anchor is deployed on the inner side of the vessel wall. When fully deployed the anchor engages both sides of the vessel wall. The inner and outer portions of the anchor are held together by a "neck" portion of the anchor which occludes the opening in the vessel wall.

Some embodiments of this invention may contain a reinforcing member in the anchor which can be used to provide an outward force against the circumference of the expanded diameter portion of the anchor so that the vessel wall is not compromised.

In some embodiments, tethers, or placement wires, may be attached to the inner portion of the button anchor and used to guide the prosthetic valve device to the location of implantation and to secure the valve device at that location.

In another embodiment, the anchors may be hooks made of shape-memory alloy materials, such as Nitinol, and may be affixed to the native anatomy as follows. The anchors are delivered to the appropriate location in the lumen using a delivery device such as a catheter. The anchors may have a delivery configuration when housed in the catheter. Once the anchors are deployed from the catheter, the anchors revert to a pre-determined shape which is curved so as to grasp the vessel wall holding the anchor in place, like a hook. The deployed (pre-determined) shape of the anchor can be semi-circular, helical, or the like. When the anchor is deployed it will be pushed into and grasp the vessel wall while it re-forms into the pre-determined shape, thus affixing the anchor to the desired location in the lumen. This embodiment may have placement wires secured to the end of the hook anchor that does not penetrate the tissue, which placement wires may be used to guide and secure the prosthetic valve device to the desired location in the lumen.

Still another embodiment of the instant invention includes anchors that are sutures, thereby also serving as the placement wires. FIG. 2 illustrates an embodiment of a placement system of the invention in which the anchors are leading sutures 46. The leading suture 46 may be attached at one end to native tissue in the lumen at the desired location of valve implantation 70 via a hook, needle, or other similar device. The other end—the free end—of the leading suture 46 may be threaded through the valve device—in the embodiment depicted in FIG. 2, a modular valve device comprising a support structure 20 and valve module 55. In this embodiment, the free ends of the leading sutures 46 are threaded through both the support structure 20 and valve module 55. The leading sutures 46 may be threaded through the valve device prior to deployment, e.g., packaged with the compressed/folded device modules in the catheter 60, or after delivery of the valve device to the body. In an alternative embodiment (not shown), the leading sutures 46 may be threaded through the delivery device or part of the devices used to expand the support structure, e.g., a balloon, or parts of devices used to release a self-expanding support structure. Where the valve device is a modular valve device, the device modules, assembled or unassembled, may be guided along the leading sutures 46 to the desired location of valve implantation 70 within a body lumen 80 with improved accuracy. Further, in cases where final deployment of the valve device at the implantation site is accomplished using a balloon catheter, the leading sutures 46 may be used to prevent migration of the valve device during balloon inflation. The proximal portion of the "free end" of the leading sutures may extend out the proximal end of the delivery device—i.e., outside the body, or may be attached to a portion of the delivery system.

The invention further provides methods for placing a prosthetic valve device in a body lumen with improved accuracy. In one embodiment, using FIG. 1A for reference, the method of placing a prosthetic valve device in a body lumen in need thereof, comprises: affixing an anchor 45 in a body lumen 80 at a location of valve implantation 70; and positioning said prosthetic valve device at said location of valve implantation 70 using said anchor 80. The anchor 45 may be connected to a placement wire 44, and the placement wire 44 may be threaded through a portion of the valve device or delivery device prior to loading the valve device into the delivery device so that a free end of the placement wire 44 exits a proximal end of said delivery device (not shown). For purposes of illustration, FIG. 1A depicts the support structure 20 of a valve device having loops as a threaded portion 21 through which the placement wires 44 are threaded. In this embodiment, the positioning step includes guiding the threaded portion 21 of the support structure 20 along the placement wire 44 to the location of valve implantation 70. In another embodiment, placement wire 44 may be threaded through a portion of the valve device after the valve device is loaded into the delivery device or after deployment of the valve device from the delivery device.

The affixing step may include affixing the anchor on the wall of the body lumen, or affixing the anchor on a proximal or distal side of a native valve leaflet. Thus for example, where the method is used in an aortic valve replacement procedure, the body lumen may be an aorta with a myocardial valve having native valve leaflets. FIGS. 1A-1C illustrate where on the native anatomy of a myocardial valve the anchors may be positioned to optimize placement of the prosthetic valve device in an aorta 81. FIG. 1A illustrates the anchors 45 fixed to a lumen wall, e.g., the aorta wall 82 immediately distal to the native valve. FIG. 1B illustrates the anchors 45 affixed to a distal surface of the native valve leaflets 76, e.g., on the aortic surface 72. FIG. 1C illustrates the anchors 45 affixed to a proximal surface of the native valve leaflets 76, e.g., on the ventricular surface 74. In an alternative embodiment, the placement wires 44 may be threaded through the proximal edge of the valve device (or support structure), and the anchors 45 may be attached immediately proximal of the native valve. In another alternative embodiment, the placement wires 44 may be threaded through a more distal portion of the valve device, the anchors 45 may be attached to the body lumen more distally of the native valve leaflets 76 than illustrated in FIG. 1A. The anchors may be used to secure the valve device to the location of implantation or valve device may further comprise separate anchoring mechanisms (note shown) for securing said valve device to the location of implantation. In such an embodiment, the method may further comprise the step of securing the valve device to the lumen wall using the anchoring mechanisms.

In still another embodiment, wherein said anchors comprise leading sutures (see FIG. 2), the leading sutures may similarly be threaded through a portion of said valve device or delivery device prior to loading said valve device into a delivery device or after deployment of the valve device. In one embodiment of the method of placing a prosthetic valve device into a lumen in need of valve replacement or implantation using the leading sutures 46 shown in FIG. 2, the method may comprise inserting percutaneously into the body lumen 80 a modular prosthetic valve system comprising a delivery device 60 containing device modules, for example a support structure 20 and a valve module 55, and a plurality of leading sutures 46, wherein each of the leading sutures 46 has a free end threaded through a portion of the device modules and exiting from a proximal end of the delivery device; advancing the delivery device to the location of valve implantation 70; attaching the leading sutures 46 to the location of valve implantation 70; retracting the delivery device from the location of valve implantation to a site of deployment; deploying the device modules; assembling the device modules into an assembled valve device; and guiding the assembled valve device along the leading sutures 46 to place the assembled valve device at said location of implantation 70. In another aspect of this embodiment, instead of exiting from the proximal end of the delivery device, the "free end" of the leading suture 46 may be attached to a portion of the delivery system. In an alternative embodiment, the leading sutures 46 may be threaded through a portion of support structure 20 and the support structure 20 may be guided to the location of implantation 70. The valve module then may be positioned and combined with the support structure 20 using pull wires or push rods (not shown). Either method may further comprise the step of affixing the assembled valve device to the location of valve implantation 70 using at least in part said leading sutures 46. As shown in FIG. 2, the leading sutures 46 may be attached to the body lumen just distal of the native valve leaflets 76 (see also FIG. 1A). Alternatively, the leading sutures 46 may be attached to the aortic surface or ventricular surface of the native valve leaflets 76, as depicted for the anchors 45 in FIGS. 1B and 1C, respectively. In another embodiment, the leading sutures 46 may be threaded through the proximal edge of the valve device and may be attached immediately proximal of the native valve leaflets 76. for example, to the ventricular surface in an aortic valve replacement (not shown). In yet another embodiment, the leading sutures 46 may be threaded through a more distal portion of the valve device, and the leading sutures 46 may be attached to the body lumen more distally of the native valve leaflets 76 than illustrated in FIG. 2. Placement of a pre-assembled valve device in accordance with the invention may proceed in a similar manner, but without the need for assembling device modules.

In an alternative embodiment of the method illustrated in FIG. 2, the leading sutures may first be affixed to the body lumen and then the valve device may be introduced. For example, the method of placing a prosthetic valve device into a lumen 80 in need of valve replacement or implantation may comprise attaching leading sutures 46 in a lumen 80 at a desired location of valve implantation 70; inserting percutaneously into a body lumen 80 a delivery device 60 containing a valve device; advancing the delivery device to a deployment site; deploying the valve device into the body lumen 80; threading the leading sutures 46 through a portion of the valve device; and guiding the valve device along the leading sutures 46 to position the valve device at the location of valve implantation 70. In an alternative embodiment, where the valve device is a modular valve device, the leading sutures may be threaded through the assembled valve device after assembly of the device modules, or the leading sutures may be threaded through the device modules after deployment and prior to assembly (not shown).

The system and method of the invention also encompass placing a pre-assembled percutaneous valve device. Thus, in a similar manner, the placement wires or leading sutures may be threaded through, for example, the frame of the percutaneous valve, i.e., the portion of the device that is expanded to seat the valve at the location of implantation. Alternatively, the placement wires or leading sutures may be threaded through the skirt or proximal (ventricular) end of the valve material. In a further alternative, the placement wires or leading sutures may be threaded through a portion of the delivery system or the components or portions of components used to expand the compressed valve device, such as for example a balloon component, or in the case of valve devices having self-expanding members, the components involved in release of the self-expanding member. The pre-assembled valve device then may be guided over the placement wires or leading sutures to the implantation spot. As with the modular valve device, one or two leading sutures or placement wires, or a ring of three or more sutures may be used.

Used with either a pre-assembled or modular percutaneous valve device, the methods of the invention improve the accuracy of placing the percutaneous valve device, and may improve the speed with which precise placement of the valve device is made.

Where the examples describe "an anchor" or "a leading suture," the embodiment may include one or more anchors or one or more leading sutures. Similarly where "a placement wire" is described, one or more may be used, but generally one placement wire is used with one appropriate type of anchor. Preferably, the anchor(s) is positioned first, and its position may be changed if necessary, prior to deployment of the valve device or device modules from the delivery device, prior to assembly of a modular valve device, or even prior to percutaneous insertion of the valve device, but always prior to placement of the valve device.

Materials useful for leading sutures in accordance with the invention include, for example, silk, metal, polyester, polypropylene, or other standard suture material known in the art. Types of polyester sutures may include, for example, 2-0 polyester (braided or unbraided). Types of polypropylene suture may include, for example, double-armed 4-0 polypropylene, 5-0 polypropylene, or 6-0 polypropylene.

Percutaneous placement of sutures may be performed by adapting methods known in the art for percutaneous closure suturing. For example, the leading suture may be placed at the site of implantation using a system comprising two catheters (a guide catheter and therapy catheter) similar to that described by Webb, J. G. et al., "Percutaneous suture edge-to-edge repair of the mitral valve," EUROINTERVENTION 5:86-89 (2009). Briefly, the guide catheter may be advanced to the target site of implantation. The "therapy catheter" (which contains one or more needles with the attached leading suture and needle catchers, an actuator trigger and an open window through which the needle and needle catcher can exit) may then be advanced through the guide catheter to the target, the window oriented toward the anchor placement site, and the actuator trigger made to drive the needle through the native tissue at the site of implantation and into the needle catcher. The therapy needle then may be sequentially rotated along its axis to one or more additional anchor sites radially displaced from the previous site, and the actuator trigger made to activate additional needles. As the therapy catheter is removed, one or more leading suture loops have been anchored at the site of valve implantation.

Other methods of attaching a suture to the site of implantation that may be adapted for use in the present invention are described, for example, in U.S. Pat. No. 6,056,760 (see, e.g., FIGS. 1, 4-9 and col. 3,II. 28-46, col. 4, II. 18-46, col. 5, I.28-col. 6, I. 6), U.S. Pat. No. 6,042,601 (see, e.g., FIGS. 1, 18-32, and col.5, II. 9-20, col. 8, I 42-col. 10, I. 32), U.S. Pat. No. 5,928,250 (see FIGS. 1-2, 8-11, and col. 3, II. 45-67, col. 5, I. 56-col. 6, I. 24, col. 6, II. 38-51), and U.S. Pat. No. 5,868,762 (see, e.g., FIGS. 1-8 and 12and col. 3, I. 66-col. 6, I. 12;col. 6, I. 53-col. 7, I. 29), which patents are incorporated herein by reference.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. A method of placing a prosthetic valve device in a body lumen in need thereof percutaneously, wherein said valve device is a modular valve device comprising a plurality of device modules, the method comprising:
affixing an anchor in a body lumen at a location of valve implantation, with the proviso that said anchor is not a leading suture;
percutaneously inserting said valve device into said body lumen;
percutaneously positioning said prosthetic percutaneous valve device at said location of valve implantation using said anchor;
wherein said anchor is connected to a placement wire; and
guiding said valve device along said placement wire to said location of valve implantation;
wherein said plurality of device modules are spatially separate during delivery and comprise a support structure and a valve module wherein each of said plurality of device modules comprises a reduced profile during delivery relative to a delivered configuration.

2. The method of claim 1, further comprising:
threading said placement wire through a portion of said valve device;
loading said valve device into a delivery system; and
guiding said threaded portion along said placement wire to said location of valve implantation.

3. The method of claim 2, wherein said threading step further includes threading said placement wire through a portion of said delivery system and attaching said placement wire thereto.

4. The method of claim 2, wherein said valve module is selected from the group consisting of: a plurality of valve sections, a leaflets substructure, and a leaflets-ring;
wherein said threaded portion of said valve device is located on said support structure.

5. The method of claim 1, said placement wire having been threaded through a portion of said valve device prior to loading said valve device into a delivery system;
wherein said positioning step includes guiding said threaded portion of said valve device along said placement wire to said location of valve implantation.

6. The method of claim 5, wherein said placement wire is threaded through a portion of said delivery system.

7. The method of any one of claims 2-6, wherein said delivery system comprises a catheter and a device for facilitating expansion of said valve device, said method further comprising:
inserting percutaneously into said body lumen said catheter containing said valve device;
advancing said catheter to a deployment site; and
deploying said valve device into said lumen.

8. The method of claim 7, wherein said placement wire is threaded through a portion of a component from the group consisting of: a device module of said modular valve device; a support structure of said modular valve device; a valve module of said modular valve device; a support structure and a valve module of said modular valve device; and said delivery system.

9. The method of claim 7, wherein said delivery system further contains said anchor and said placement wire, said placement wire being attached at one end to said anchor, said placement wire also being threaded through a portion of said valve device;
said affixing step occurring after said advancing step, and including
(i) moving said catheter towards said location of valve implantation;
(ii) affixing said anchor to said location of valve implantation; and
(iii) retracting said catheter from said location of valve implantation to said site of deployment;
said positioning step including guiding said threaded portion of said valve device along said placement wire to said location of implantation.

10. The method of claim 9, wherein said threaded portion of said valve device is located on said support structure.

11. The method of claim 2 or 5, wherein said anchor is selected from the group consisting of: a hook; a button-type device; a rivet-type device; and interconnecting geometries.

12. The method of claim 1, wherein said body lumen is an aorta, and said affixing step includes attaching said anchor to an aorta wall.

13. The method of claim 1, wherein said body lumen is an aorta having native valve, said native valve comprising native valve leaflets having aortic surfaces;
and wherein said affixing step includes attaching said anchor to said aortic surfaces of said native valve leaflets.

14. The method of claim 1, wherein said body lumen is an aorta having native valve, said native valve comprising native valve leaflets having ventricular surfaces; and wherein said affixing step includes attaching said anchor to said ventricular surfaces of said native valve leaflets.

15. The method of claim 1, further comprising:
securing said valve device to said location of valve implantation using at least in part said anchor.

16. A method of placing a prosthetic valve device in a body lumen in need thereof percutaneously, wherein said valve device is a modular valve device comprising a plurality of device modules, the method comprising:
affixing an anchor in a body lumen at a location of valve implantation, wherein said anchor is an anchor docking apparatus;
inserting percutaneously into said body lumen a delivery device containing a valve device comprising an anchor interface unit, wherein said anchor interface unit is configured to engage with said anchor docking apparatus;
advancing said delivery device to said location of valve implantation;
deploying said valve device from said delivery device; and
percutaneously positioning said valve device at said location of valve implantation using said anchor;

wherein said positioning step includes engaging said anchor interface unit and said anchor docking apparatus;

wherein said plurality of device modules are spatially separate during delivery and comprise a support structure and a valve module and wherein each of said plurality of device modules comprises a reduced profile during delivery relative to a delivered configuration.

17. The method of claim 16, wherein said device modules further comprise a plurality of valve sections, said anchor interface unit being attached to said support structure;
   said deploying step further comprising:
   i) deploying said support structure so as to engage said anchor interface unit and said anchor docking apparatus and place said support structure at said location of valve implantation; and
   ii) deploying said plurality of valve sections;
   said method further comprising:
      assembling said valve sections to form a valve assembly; and
      combining said valve assembly and said support structure to form an assembled valve device.

18. The method of claim 16, wherein said device module is selected from the group consisting of a leaflet substructure and a leaflets-ring, said anchor interface unit being attached to said support structure; said deploying step further comprising:
   i) deploying said support structure so as to engage said anchor interface unit and said anchor docking apparatus and place said support structure at said location of valve implantation; and
   ii) deploying said valve module;
   said method further comprising:
      assembling said valve module into a working configuration valve component; and
      combining said valve component and said support structure to form an assembled valve device.

19. The method of claim 16, wherein said anchor is selected from the group consisting of: a hook, a button-type device, a rivet-type device, and interconnecting geometries.

20. The method of claim 16, wherein the affixing step comprises penetrating tissue of said body lumen with said anchor.

21. A method of placing a prosthetic valve device in a body lumen in need thereof percutaneously, wherein said valve device is a modular valve device comprising a plurality of device modules, the method comprising:
   affixing an anchor in a body lumen at a location of valve implantation, with the proviso that said anchor is not a leading suture;
   percutaneously inserting said valve device into said body lumen;
   percutaneously positioning said valve device at said location of valve implantation using said anchor, wherein said anchor is connected to a placement wire;
   guiding said valve device along said placement wire to said location of valve implantation; and
   assembling said device modules into an assembled valve device in vivo;
   wherein said modular valve device comprises a reduced profile during delivery relative to a delivered configuration.

22. A method of placing a prosthetic valve device in a body lumen in need thereof percutaneously, wherein said valve device is a modular valve device comprising a plurality of device modules, the method comprising:
   affixing an anchor in a body lumen at a location of valve implantation, wherein said anchor is an anchor docking apparatus;
   inserting percutaneously into said body lumen a delivery device containing a valve device comprising an anchor interface unit, wherein said anchor interface unit is configured to engage with said anchor docking apparatus;
   advancing said delivery device to said location of valve implantation;
   deploying said valve device from said delivery device;
   assembling said device modules into an assembled device in vivo; and positioning said valve device at said location of valve implantation using said anchor, wherein said positioning step includes engaging said anchor interface unit and said anchor docking apparatus;
   wherein said modular valve device comprises a reduced profile during delivery relative to a delivered configuration.

* * * * *